(12) United States Patent
Zhao et al.

(10) Patent No.: US 11,035,495 B2
(45) Date of Patent: Jun. 15, 2021

(54) FLOW CONTROL MECHANISM AND SYSTEM COMPRISING THE MECHANISM

(71) Applicant: HELIXGEN (GUANGZHOU) CO., LTD., Guangdong (CN)

(72) Inventors: Tianxian Zhao, Guangdong (CN); Qing Zeng, Guangdong (CN); Zhongman Zhang, Guangdong (CN); Amer El-Hage, Menlo Park, CA (US)

(73) Assignee: HELIXGEN (GUANGZHOU) CO., LTD., Guangdong (CN)

( * ) Notice: Subject to any disclaimer, the term of this patent is extended or adjusted under 35 U.S.C. 154(b) by 229 days.

(21) Appl. No.: 16/315,535

(22) PCT Filed: Jul. 6, 2016

(86) PCT No.: PCT/CN2016/088759
§ 371 (c)(1),
(2) Date: Jan. 4, 2019

(87) PCT Pub. No.: WO2018/006286
PCT Pub. Date: Jan. 11, 2018

(65) Prior Publication Data
US 2019/0301640 A1    Oct. 3, 2019

(51) Int. Cl.
*F16K 99/00* (2006.01)
*C12M 1/00* (2006.01)
(Continued)

(52) U.S. Cl.
CPC ............ *F16K 99/0028* (2013.01); *C12M 1/00* (2013.01); *C12Q 1/06* (2013.01); *F16K 99/0034* (2013.01);
(Continued)

(58) Field of Classification Search
CPC ............ F16K 99/0028; F16K 99/0003; F16K 99/0001; C12M 1/00; C12Q 1/06
(Continued)

(56) References Cited

U.S. PATENT DOCUMENTS 3,933,165 A * 1/1976 Budzak ............... G01N 31/005
137/625.48
4,676,274 A   6/1987 Brown
(Continued)

FOREIGN PATENT DOCUMENTS

CN         1671467 A      9/2005
CN       101563562 A     10/2009
(Continued)

OTHER PUBLICATIONS

First Non-Final Office Action issued in corresponding TW Application No. 106145431 dated Sep. 14, 2018 (with English translation).
(Continued)

*Primary Examiner* — Christine T Mui
(74) *Attorney, Agent, or Firm* — Muncy, Geissler, Olds & Lowe, P.C.

(57) ABSTRACT

A flow control mechanism and a system comprising the mechanism, specifically relating to a microflow control mechanism and system. The mechanism comprises a base and a constant volume mechanism. The base and the constant volume mechanism are dynamically connected to form two or more relative activity states, comprising a first relative state and a second relative state. A fluid input end and a fluid receiving end are provided on the base. The constant volume mechanism is provided with a constant volume pipeline. In the first relative state, the fluid input end communicates with the constant volume pipeline. In the second relative state, the constant volume pipeline commu-
(Continued)

nicates with the fluid receiving end. The microflow control mechanism and system can achieve precise micro-scale fluid flow control, and have a simple structure.

20 Claims, 7 Drawing Sheets (51) Int. Cl.
*C12Q 1/06* (2006.01)
*B01L 3/00* (2006.01)

(52) U.S. Cl.
CPC . *B01L 3/502738* (2013.01); *F16K 2099/0084* (2013.01)

(58) Field of Classification Search
USPC .......................................... 422/502, 500, 50
See application file for complete search history.

(56) References Cited

U.S. PATENT DOCUMENTS

| 6,096,276 | A | * | 8/2000 | Laursen | ............... | B01J 19/0046 |
|---|---|---|---|---|---|---|
| | | | | | | 422/540 |
| 6,632,404 | B1 | | 10/2003 | Freitag et al. | | |
| 9,027,929 | B2 | * | 5/2015 | Picha | ................. | G01N 35/1097 |
| | | | | | | 277/314 |
| 2002/0155032 | A1 | | 10/2002 | Liu et al. | | |
| 2003/0170131 | A1 | | 9/2003 | Zare et al. | | |
| 2007/0154355 | A1 | * | 7/2007 | Berndt | ............. | B01L 3/502715 |
| | | | | | | 422/400 |
| 2008/0160603 | A1 | * | 7/2008 | Sundararajan | ...... | F16K 99/0015 |
| | | | | | | 435/288.5 |

FOREIGN PATENT DOCUMENTS

| CN | 101850231 A | 10/2010 |
|---|---|---|
| CN | 102278293 A | 12/2011 |
| JP | H 5-142117 A | 6/1993 |
| JP | 2005-83510 A | 3/2005 |

OTHER PUBLICATIONS

Second Non-Final Office Action issued in corresponding TW Application No. 106145431 dated Feb. 18, 2019 (with English translation).

* cited by examiner

Fig. 10C

FLOW CONTROL MECHANISM AND SYSTEM COMPRISING THE MECHANISM

TECHNICAL FIELD

The present invention relates to the field of fluid control devices, in particular, to a fluid control mechanism and a system comprising the same, and more particularly, to a microfluidic mechanism and a system.

BACKGROUND ART

In the technical field of biological testing, since a substance to be tested is generally small in volume and generally at a microliter level, relatively accurate quantification is required. For example, in the field of molecular biological diagnosis, in order to perform multi-target DNA detection at the same time, it is necessary to dilute a DNA sample and distribute the DNA sample into a plurality of PCR reaction test tubes for fluorescence detection after the PCR cycle. Sample treatment procedures in such test process are relatively cumbersome, time-consuming and error-prone. With the development of microfluidic technologies and other related technologies, the DNA detection steps above, including all sample treatment procedures can be basically integrated into a tiny plastic cartridge and fully automated. In the above sample treatment procedures, the most critical difficulty is how to accurately dispense the trace amount of DNA sample into a plurality of reaction chambers.

In recent years, researchers have conducted much research on how microfluidic system devices control and reduce the analytical sample volumes of fluids.

Chinese patent CN101563562A discloses a microfluidic device, which achieves precise microfluidic control through a structural unit designing an optimized dead volume in order to obtain an accurate small volume of fluid sample. The microfluidic device includes a substrate provided with micro-channels, a flexible membrane, and a brake piece; a temporary passage is formed by the flexible membrane covering a valve region; a fluid is guided between the region of a lower surface of the substrate and an upper surface of the flexible membrane; the brake member moves toward the lower surface of the substrate, leading to valve action; the lower surface of the substrate moves reversely to release an indoor space; and the flexible membrane can be engaged into the space to form the temporary passage. However, the structure of the microfluidic device itself is still not sufficiently simplified, and the interference of bubbles cannot be eliminated in a fluid control process of a liquid fluid sample.

SUMMARY OF THE INVENTION

An object of the present invention is to provide a fluid control mechanism which is simple in structure.

Another object of the present invention is to provide a fluid control mechanism which saves the volume.

Another object of the present invention is to provide a fluid control mechanism which is accurate in quantification.

A further object of the present invention is to provide a fluid control mechanism which is simple in structure and accurate in quantification.

A further object of the present invention is to provide a fluid control mechanism which saves the volume and is accurate in quantification.

A further object of the present invention is to provide a system comprising the fluid control mechanism.

A further object of the present invention is to provide a microfluidic system applied to quantitative sampling or detection of biological samples.

A further object of the present invention is to provide a microfluidic system applied to PCR detection.

The fluid control mechanism particularly relates to a microfluidic mechanism.

The invention is realized by the following technical solutions:

a fluid control mechanism, particularly a microfluidic mechanism, including: a base and a quantitative mechanism which are movably connected to form two or more relative motion states including a first relative state and a second relative state; a fluid input end and a fluid receiving end are disposed on the base; the quantitative mechanism is provided with a quantitative pipeline; when in the first relative state, the fluid input end is connected with the quantitative pipeline; when in the second relative state, the quantitative pipeline is connected with the fluid receiving end; and in a process of switching from the first relative state to the second relative state, two ends of the quantitative pipeline are kept sealed.

The quantitative mechanism is provided with at least one surface fitting with the base; the fluid input end and the fluid receiving end are disposed at the fitting surfaces of the base and of the quantitative mechanism; and preferably, the fitting surfaces are smooth.

More preferably, the base is divided into two portions; the quantitative mechanism is provided with two surfaces fitting with the base; and in the process of switching from the first relative state to the second relative state, the two ends of the quantitative pipeline are subjected to covered fitting by the surfaces of the base and thus kept sealed.

Further, when in the first relative state, the fluid input end is seamlessly connected with the quantitative pipeline; and when in the second relative state, the quantitative pipeline is seamlessly connected with the fluid receiving end.

The fluid input end above refers to a fluid input port, or a port having an extending pipeline; and when in the first relative state, a fluid flows into the quantitative pipeline from such fluid input end.

Similarly, the fluid receiving end above refers to a fluid receiving port, or a port having an extending pipeline; and when in the second relative state, the fluid in the quantitative pipeline flows out via such fluid receiving end.

In addition, when in the first relative state, the quantitative pipeline is not connected with the fluid receiving end; and when in the second relative state, the quantitative pipeline is not connected with the fluid input end.

The non-connection above can be realized by staggered arrangement between the fluid input end and the fluid receiving end; and the staggered arrangement means that in any relative displacement state, a connecting line between the fluid input end and the fluid receiving end is not overlapped with the quantitative pipeline.

As a particularly preferred embodiment of the invention: the base is provided with two or more fluid input ends; the quantitative mechanism is provided with two or more quantitative pipelines; when in the first relative state, the two or more fluid input ends form a tandem connection passage through mediation of the quantitative pipelines; preferably, the fluid input ends are seamlessly connected with the quantitative pipelines in a alternately arrangement when the tandem connection passage is formed; and this can be realized by, for example, equidistant arrangement of similar pipelines or ports.

In order to achieve that two ends of the quantitative pipelines are kept sealed in the process of switching from the first relative state to the second relative state, at this time, preferably, the two ends of the quantitative pipelines are subjected to covered fitting by the surfaces of the base and thus kept sealed; in the switching process, a relative displacement trajectory produced by the fitting surfaces of the quantitative pipes and the base does not pass through any gap or clearance or cavity, that is to say, the trajectory does not pass through any other fluid input end, the first gap or clearance or cavity where the trajectory reaches is the fluid receiving end, and at this time, the fluid control mechanism is already in the second relative state; and this can be achieved by alternately arranging the fluid input ends and the fluid receiving ends, particularly, alternately arranging the fluid input ends and the fluid receiving ends one after another in a direction of the relative motion trajectory.

Certainly, as a non-preferred but alternative solution, if in the process of switching from the first relative state to the second relative state, the trajectory passes through a certain cavity, for example, a certain fluid input end, then, the fluid input end needs to be temporarily closed first to prevent the fluid in the quantitative pipelines from leaking from other gaps or clearances or cavities when the fluid reaches the corresponding fluid receiving ends.

At this time, the fluid input ends (preferably having extending pipes) and the quantitative pipelines are connected in series in a mutually spaced manner to form a tandem connection passage, at this point, the flow control mechanism is in a fluid charging state (liquid filling state), and the fluid needs to be quantitatively sampled continuously passes through a plurality of fluid input ends (extending pipes) and the quantitative pipelines which are arranged in a spaced manner in the same single passage.

After completing the fluid charging process (preferably charging the entire tandem connection passage and a portion of the fluid overflowing from the end (the end is directly or indirectly identical to the outside) of the tandem connection passage to the waste liquid container), the flow control mechanism is switched to the second relative state.

In the second relative state, the quantitative pipelines are seamlessly connected with the corresponding fluid receiving ends (preferably having extending pipes) to form quantitative pipeline plus fluid receiving end combinations, two or more quantitative pipeline plus fluid receiving end combinations are arranged side by side, and the various combinations are not connected with one another.

Such structure is very advantageous for achieving precise microfluidics, attributing to that the microfluidic mechanism is generally configured to be a small volume application, such as a microfluidic chip, and thus has a limited volume for accommodation.

In the application of liquid fluid control technologies, during liquid charging (whether liquid pushing or suction), the portion of the liquid output first contains bubbles easily, and since the volume of the liquid sampled by the microfluidic technology is very small, the bubbles will have great influence on the accuracy of the sampling quantity. In order to reduce such influence, it is preferable to discard a portion of the liquid at the front end when taking liquid in each tube, thus requiring more liquid supply and a relatively large waste liquid storage space. However, the microfluidic mechanism is generally configured to be the small volume application, such as the microfluidic chip, and thus has a limited volume for accommodation.

While due to the tandem connection passage of the present invention, the filling of the multi-stage quantitative pipelines can be realized continuously in one-time liquid pushing or suction process, so that in the multi-tube liquid taking, only a section of the front-end liquid needs to be discarded, which greatly reduces the demand for liquid supply and the waste storage space (because only one waste liquid cylinder is required to receive the section of the front-end liquid at this time, without requiring a plurality of waste liquid cylinders to receive a plurality of sections of front-end liquid).

Theoretically, the more the tandem quantitative pipelines are, the more favorable it is to eliminate the influence of bubbles and to save the volume.

As an illustrative example, the number of the quantitative pipelines or the fluid input ends corresponding to the quantitative pipelines provided herein may be 3, 4, 5, 6, 7, 8, 9, 10, or more.

The cross-sectional areas of the quantitative pipelines are 0.01-100 mm$^2$.

The fluid input ends and the fluid receiving ends are disposed at the fitting surfaces of the base and of the quantitative mechanism.

Preferably, in the process of switching between the first relative state and the second relative state through motion, the quantitative pipelines are kept sealed by the connected surfaces of the base and the quantitative mechanism.

Preferably, sealing components are disposed at the two ends of the quantitative pipelines, so that seamless connection is realized better in a process of connecting with the fluid receiving ends or the fluid receiving ends, and a seamless sealing state is kept all the time advantageously in the switching process.

Further, the fluid input ends are connected with a fluid storage device; and the fluid storage device is used for storing a fluid to be subjected to quantitative diversion/quantitative sampling.

Further, the fluid receiving ends are connected with fluid receiving devices. When switching to the second relative state, the quantitative pipelines are not connected with the fluid input ends any more, but shift relatively to be connected with the fluid receiving devices, and at this time, under action of gravity or applied external force (for example, pushing force or suction force), the fluid flows from the quantitative pipelines to the fluid receiving devices via the fluid receiving ends. Generally, the fluid receiving devices are places where reaction/detection is carried out after samples are added quantitatively, or places where the samples are mixed with other samples.

Further, the fluid control mechanism is further provided with one or more first differential pressure mechanisms; and when the fluid control mechanism is in the first relative state, the one or more first differential pressure mechanisms allows/allow pressure at ends, connected with the fluid input ends, of the quantitative pipelines to be greater than pressure at ends, far away from the fluid input ends, of the quantitative pipelines, thereby forming pressure differences.

Preferably, the one or more first differential pressure mechanisms is/are disposed on the base; and more preferably, the one or more first differential pressure mechanisms is/are a pressurizing device or pressurizing devices (for example, pumps and pistons) disposed at the ends of the fluid input ends, or a negative pressure device or negative pressure devices (for example, vacuum pumps) disposed at the ends, far away from the fluid input ends, of the quantitative pipelines.

Or, the fluid control mechanism is further provided with second differential pressure mechanisms; and when the fluid control mechanism is in the second relative state, the second differential pressure mechanisms allow pressure at ends, connected with the fluid receiving ends, of the quantitative pipelines to be less than pressure at ends, far away from the fluid receiving ends, of the quantitative pipelines, thereby forming pressure differences.

Preferably, the second differential pressure mechanisms are disposed on the base; and more preferably, the second differential pressure mechanisms are negative pressure devices disposed at the fluid receiving ends, or pressurizing devices (for example, pumps and pistons) disposed at the ends, far away from the fluid receiving ends, of the quantitative pipelines.

When either the first differential pressure mechanisms or the second differential pressure mechanisms exist in the system, either the tandem connection passage formed in the first relative state or the quantitative pipelines in the second relative state are in a perpendicular direction, so that a pipeline passage in the perpendicular direction achieves fluid flowing under the action of gravity. However, preferably, the first differential pressure mechanisms and the second differential pressure mechanisms exist at the same time.

To facilitate the flowing of the fluid, when in the first relative state, an exhaust port is disposed at a tail of an end, far away from the fluid input end, of the quantitative pipeline; preferably, the exhaust port is provided with a self-sealing membrane; and more preferably, a waste liquid container is disposed in front of the exhaust port.

In an embodiment of the invention, the motion is translation; and the tandem connection passage penetrates through the base and the quantitative mechanism to form a tandem connection channel.

As a preferred embodiment of the invention, the base of the invention includes a first base and a second base; the quantitative mechanism is located between the first base and the second base; and the fluid input ends have extending fluid input pipelines.

Preferably, the fluid control mechanism includes a plurality of fluid input ends and a plurality of quantitative pipelines; the plurality of fluid input ends are alternately disposed on the first base and the second base in sequence; and when in the first relative state, the extending fluid input pipelines of the plurality of fluid input ends, through mediation of the quantitative pipelines, penetrate through the first base, the quantitative mechanism and the second base to form a sinuous channel (seamlessly connected tandem connection channel).

In the examples having a plurality of fluid input ends, a connecting line between the tangent point of the extending fluid input pipeline of the fluid input end not located at the front-most end and the fitting surface (the surface, corresponding to the fluid input end, of the base), and the previous fluid input end is located in a direction parallel to the quantitative pipeline.

When the quantitative mechanism moves in a direction perpendicular to the quantitative pipelines, the switching between the first relative state and the second relative state of the flow control mechanism can be achieved; and this embodiment is the most preferred embodiment, of which a structure and a motion mechanism are the most simplified, and the fluid control mechanism can be made into a small-volume fluid control chip.

In another embodiment of the invention, the motion is rotational motion; the quantitative mechanism is two or more rotary discs embedded into the base; the thicknesses of the rotary discs are greater than the diameters of the quantitative pipelines; preferably, an annular mutual fitting surface is formed between each rotary disc sand the base, the annular surfaces herein refer to side surfaces of cylinders, and the fitting surfaces are preferably smooth;

preferably, centers of all the rotary discs are arranged linearly; the quantitative pipelines are disposed at center lines of the rotary discs, and when the rotary discs are rotated to allow the quantitative pipelines to be overlapped with a straight line, the fluid control mechanism is in the first relative state;

when the rotary discs are rotated to allow the quantitative pipelines to be not overlapped with said straight line, the fluid control mechanism is in the second relative state;

and more preferably, when the quantitative pipelines are perpendicular to said straight line, the fluid control mechanism is in the second relative state.

In another embodiment of the invention, the fluid control mechanism has n bases and (n−1) quantitative mechanisms which are arranged alternately; (2n−2) mutual fitting surfaces are formed between the bases and the quantitative mechanisms; the fluid control mechanism is provided with one or more fluid control groups; each fluid control group is provided with:

at least (n−1) fluid input ends distributed on the (n−1) bases one by one, at least (n−1) fluid receiving ends distributed on the (n−1) bases one by one, and quantitative pipelines disposed on each quantitative mechanism one by one;

the quantitative pipelines in the same fluid control group are arranged in a same straight line;

in the bases not at two ends, each fluid input end has a fluid input pipeline penetrating through the base where this fluid input end is located, and tangent points of the fluid input pipelines and the fitting surfaces are located in one straight line parallel to the directions of the quantitative pipelines; and thus, when in the first relative state, all the fluid input ends (fluid input pipelines) form a tandem connection passage through mediation of the plurality of quantitative pipelines.

A connecting line of the fluid receiving ends is also in one straight line parallel to the directions of the quantitative pipelines.

Preferably, the plurality of quantitative mechanisms have unified motion mechanisms capable of driving the plurality of quantitative mechanisms to make translational motion at the same time.

The invention further provides a system including the fluid control mechanism. The fluid input ends of the system are connected with a fluid storage device; and the fluid storage device is further connected with a pretreatment chamber for pretreatment on a fluid.

Preferably, a pressurizing device is disposed at an end, far away from the fluid storage device, of the pretreatment chamber, or a negative pressure device is disposed at an end, far away from the pretreatment chamber, of the fluid storage device, so that it is more conducive to introducing the pretreated fluid into the fluid storage device.

Preferably, the fluid storage device and the pretreatment chamber are both located on the base.

Further preferably, the pretreatment chamber is connected with the fluid storage device through a pipeline; more preferably, the pretreatment chamber is connected with the fluid storage device through a pipeline provided with a filter mechanism; and the filter mechanism is a filter sheet, a filter mesh, a filter membrane, filter gel, or a filter column, etc.

Further preferably, the pretreatment chamber is provided with a heating device.

In the embodiment including the first base and the second base, the pretreatment chamber and the fluid storage device are located at the first base or the second base at the same time; or, the pretreatment chamber and the fluid storage device are located at the first base and the second base respectively; the pretreatment chamber is connected with the quantitative mechanism through the pipeline disposed at the quantitative mechanism; and the pipeline is one of the quantitative pipelines or an independent other pipeline.

Further preferably, the fluid receiving ends are further connected with fluid receiving devices, namely, reaction chambers; and preferably, the reaction chambers are pre-filled with pre-filling materials, so that reaction starts immediately after the fluid is quantitatively conveyed to the reaction chambers through the fluid control mechanism.

The invention further provides an application of the system above. The system is used for quantitative sampling or detection of biological samples.

Preferably, the system is used for quantitative sampling or detection of PCR.

More preferably, the reaction chambers are pre-filled with a PCR reaction reagent.

The invention has the advantages that the microfluidic mechanism and the system can accurately control a trace fluid flow and are simple in structure.

DETAILED DESCRIPTION OF THE INVENTION

The invention will be further described in combination with accompanying drawings and specific examples.

Example 1

Figure 1:
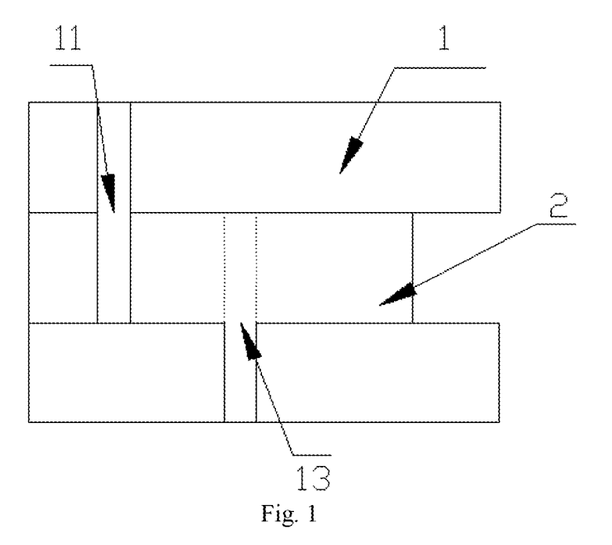
FIG. 1 is a structural schematic diagram of Example 1 of a microfluidic mechanism of the present invention.

FIG. 1 is an example of a core portion of a microfluidic mechanism of the present invention, including a base 1 and a quantitative mechanism 2 which are movably connected; the base 1 includes a first base (upper base) and a second base (lower base); the quantitative mechanism 2 is between the upper base and the lower base, and can horizontally move along a fitting surface by virtue of a sliding mechanism such as a sliding rail to achieve the switching between a first relative state and a second relative state; an upper surface of the quantitative mechanism 2 fits with a lower surface of the upper base; a lower surface of the quantitative mechanism 2 fits with an upper surface of the lower base; the fitting surfaces are smooth; a quantitative pipeline 21 penetrates through the upper surface and the lower surface of the quantitative mechanism 2 is perpendicularly disposed in the quantitative mechanism 2; the quantitative pipeline 21 is a straight pipe; a fluid input end 11 is disposed at the lower surface of the upper base; a fluid receiving end 13 is disposed at the upper surface of the lower base; the fluid input end 11 has a pipeline extending upward; the fluid receiving end 13 has a pipeline extending downward; and the fluid input end 11 and the fluid receiving end 13 are disposed in a staggered manner so that a connecting line between the fluid input end 11 and the fluid receiving end 13 is not overlapped with the quantitative pipeline 21 when the quantitative mechanism 2 slides to any position.

During operation, when the fluid input end 11 is connected with the quantitative pipeline 21, the first relative state is formed, a fluid fills in from the fluid input end 11 via the quantitative pipeline 21, then the quantitative mechanism 2 slides, the quantitative pipeline 21 filled with the fluid is pushed to move till the quantitative pipeline 21 is connected with the fluid receiving end 13, at this time, the microfluidic mechanism is in the second relative state, and the fluid flows out via the fluid receiving end 13 by virtue of externally applied pressure.

In a process of pushing along a path, two ends of the quantitative pipeline 21 are respectively fitted with the lower surface of the upper base and the upper surface of the lower base in a covered manner all the time, thus keeping the two ends sealed. In a preferred embodiment, sealing components (not shown in FIG. 1) are disposed at the two ends of the quantitative pipeline 21. In the second relative state, an end of the quantitative pipeline 21 is connected with an inlet of the fluid receiving end 13, so that the fluid reaches a fluid receiving device through the fluid receiving end 13.

This example may have a variety of transformation modes. For example, up-and-down arrangement of the first base and the second base is turned into left-and-right arrangement. Or for example, either the first base or the second base is omitted, while the fluid input end and the fluid receiving end 13 are disposed on the same base, after the quantitative pipeline is filled with the fluid and the second relative state is reached, the fluid is reversely returned and conveyed to the fluid receiving end 13 preferably under the action of a pressurizing pump or a vacuum pump (as a second differential pressure mechanism in the description, not shown in the figure, referring to Example 2).

Example 2

Figure 2:
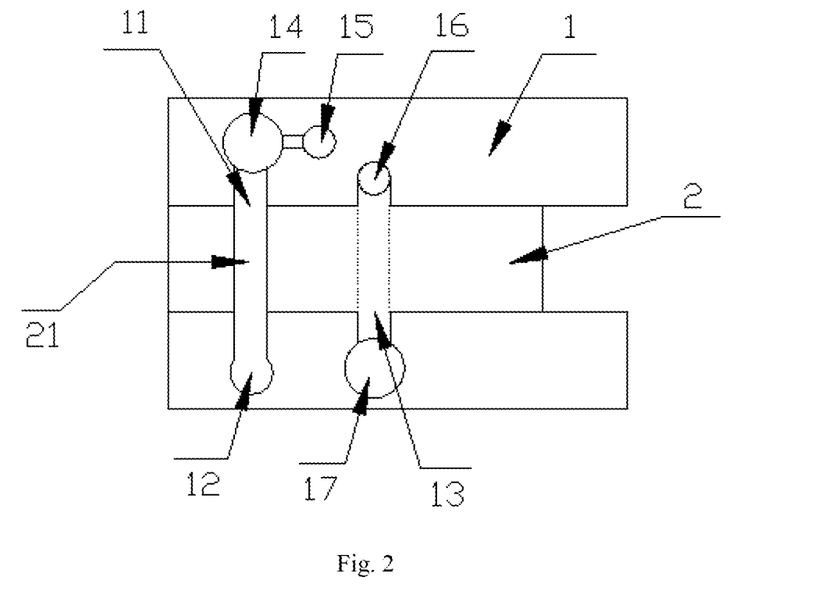
FIG. 2 is a structural schematic diagram of Example 2 of the microfluidic mechanism of the present invention.

As shown in FIG. 2, Example 2 is further provided with a fluid storage device, a waste liquid container and differential pressure mechanisms on the basis of a core mechanism of Example 1.

On the basis of Example 1, in the upper base, the pipeline of the fluid input end 11 is connected with the fluid storage device 14; the waste liquid container 12 is disposed at a position, corresponding to the fluid input end 11, in the lower base; the fluid storage device 14 is provided with a pump as the first differential pressure mechanism 15; in the lower base, a pipeline of the fluid receiving end 13 is connected with the fluid receiving device 17; and a pump is correspondingly disposed at a portion, corresponding to the fluid receiving device 17 in a perpendicular direction, of the upper base and acts as the second differential pressure mechanism 16.

Operation processes of the microfluidic mechanism are as follows: when the quantitative mechanism 2 slides to a position where the fluid input end 11 is connected with the quantitative pipeline 21, the first relative state is formed, and at this time, under the action of the pump, the fluid in the fluid storage device 14 is input into the quantitative pipeline 21 through the fluid input end 11 and fills the quantitative pipeline 21 up, and an excess portion of the fluid flows into the waste liquid container 12.

Subsequently, the quantitative mechanism 2 slides again, the quantitative pipeline 21 filled with the fluid is pushed to move till the quantitative pipeline 21 is connected with the fluid receiving end 13, and at this time, the microfluidic mechanism is in the second relative state; and in the second relative state, a lower end of the quantitative pipeline 21 is connected with the fluid receiving end 13, an upper end of the quantitative pipeline 21 corresponds to the second differential pressure mechanism 16 of the upper base, and at this time, preferably under the action of the pump, the fluid is pressed out and output to the fluid receiving device 17 through the fluid receiving end 13.

Example 3

Figure 3:
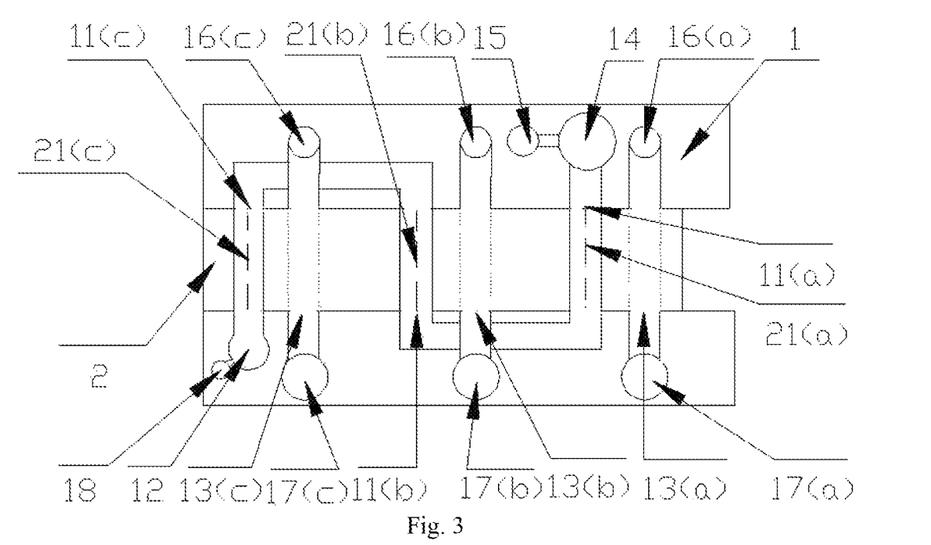
FIG. 3 is a structural schematic diagram of Example 3 of the microfluidic mechanism of the present invention.

FIG. 3 is a preferred example of the core portion of the microfluidic mechanism of the present invention, which differs from Example 1 in that the quantitative mechanism 2 is provided with three quantitative pipelines 21 (indicated as 21(a), 21(b) and 21(c) in FIG. 3); the base 1 is provided with three fluid input ends 11 (indicated as 11(a), 11(b) and 11(c) in FIG. 3); the three fluid input ends 11 are all disposed on the fitting surfaces of the base 1 and the quantitative mechanism 2 and have pipelines extending away from the surfaces; the three fluid input ends 11 are alternately disposed on the first base (upper base) and the second base (lower base) in sequence, for example, the first fluid input end 11(a) is disposed on the upper base, then the second fluid input end 11(b) is disposed on the lower base, and the third fluid input end 11(c) is disposed on the upper base, and so on; a center virtual perpendicular line (shown as a long dotted line in FIG. 3) of each fluid input end 11 forms a virtual intersected point on the upper surface of the lower base; one fluid receiving end 13 (indicated as 13(a), 13(b) and 13(c) in FIG. 3) is disposed on a right side of each intersected point; and the distance between each fluid receiving end 13 and the intersected point at the left of this fluid receiving end 13 is identical.

With regard to the various quantitative pipelines 21 (indicated as 21(a), 21(b) and 21(c) in FIG. 3) on the quantitative mechanism 2, the distance between every two adjacent quantitative pipelines 21 is equal to the distance between the two corresponding adjacent fluid receiving ends 13 (indicated as 13(a), 13(b) and 13(c) in FIG. 3).

During operation, in an initial state, the quantitative mechanism 2 is located at a position where the various quantitative pipelines 21 are in butt joint with the various fluid input ends 11; as shown in FIG. 3, the pore sizes of the various quantitative pipelines 21 are identical with the sizes of openings of the corresponding fluid input ends 11, and the quantitative pipelines 21 correspond to the openings of the corresponding fluid input ends 11 in position; at this time, the first fluid input end 11(a) is connected with an upper end of the first quantitative pipeline 21(a), and the second fluid input end 11(b) is connected with a lower end of the first quantitative pipeline 21(a) at an end of an extending pipeline of the lower base; the second fluid input end 11(b) is connected with a lower end of the second quantitative pipeline 21(b); the third fluid input end 11(c) is connected with an upper end of the second quantitative pipeline 21 at an end of an extending pipeline on the upper base; and a system is in the first relative state, that is, at this time, the three fluid input ends 11, the extending pipelines of the three fluid input ends 11 and the plurality of quantitative pipelines 21 are already arranged in a spaced manner to form a tandem connection passage, so that the system carries out continuous fluid charging, namely fluid charging as a full line mode shown in FIG. 3.

Corresponding to the fluid input end 11(c) at the end (the leftmost side as shown in FIG. 3), the waste liquid container 12 is disposed on a portion, on the opposite side of the fluid input end 11(c), of the lower base, and provided with an exhaust port 18; the extending pipeline of the first fluid input end 11(a) is connected with the fluid storage device 14; the fluid storage device 14 is connected with the pressurizing pump as the first differential pressure mechanism 15; in the lower base, a pipeline of each fluid receiving end 13 (indicated as 13(a), 13(b) and 13(c) in FIG. 3) is connected with one fluid receiving device 17 (indicated as 17(a), 17(b) and 17(c) in FIG. 3); and pumps are correspondingly disposed on portions, corresponding to the fluid receiving devices 17 in perpendicular directions, of the upper base, and act as second differential pressure mechanisms (indicated as 16(a), 16(b) and 16(c) in FIG. 3).

Operation processes of the microfluidic mechanism are as follows: when the quantitative mechanism 2 slides to be in butt joint with the fluid input ends 11 (at positions shown as full lines in FIG. 3) and the three fluid input ends 11, the extending pipelines of the three fluid input ends 11 and the plurality of quantitative pipelines 21 are arranged in a spaced manner, the first relative state is formed; and at this time, under the action of the pressurizing pump as the first differential pressure mechanism 15, the fluid in the fluid storage device 14 flows through the first fluid input end 11(a), the first quantitative pipeline 21(a), the second fluid input end 11(b), the second quantitative pipeline 21(b), the third fluid input end 11(c) and the third quantitative pipeline 21(c) and fills the tandem connection passage up, and an excess portion of the fluid flows into the waste liquid container 12.

Subsequently, the quantitative mechanism 2 slides again, the three quantitative pipelines 21 filled with the fluid are pushed to move till the quantitative pipeline 21(a) is connected with the fluid receiving end 13(a), the quantitative pipeline 21(b) is connected with the fluid receiving end 13(b) and the quantitative pipeline 21(c) is connected with the fluid receiving end 13(c) (that is, the quantitative pipelines 21 move to positions shown as short dotted lines in FIG. 3), and at this time, the microfluidic mechanism is in the second relative state; in the second relative state, a lower end of each quantitative pipeline 21 is connected with the corresponding fluid receiving end 13, and upper ends of the quantitative pipelines 21 correspond to the pumps (indicated as 16(a), 16(b) and 16(c) in FIG. 3) as the second differential pressure mechanisms 16 of the upper base; and under the action of the pumps, the fluid is pressed out and output to the fluid receiving devices 17 (indicated as 17(a), 17(b) and 17(c) in FIG. 3) through the corresponding fluid receiving ends 13 (indicated as 13(a), 13(b) and 13(c) in FIG. 3).

Example 4

Figure 4:
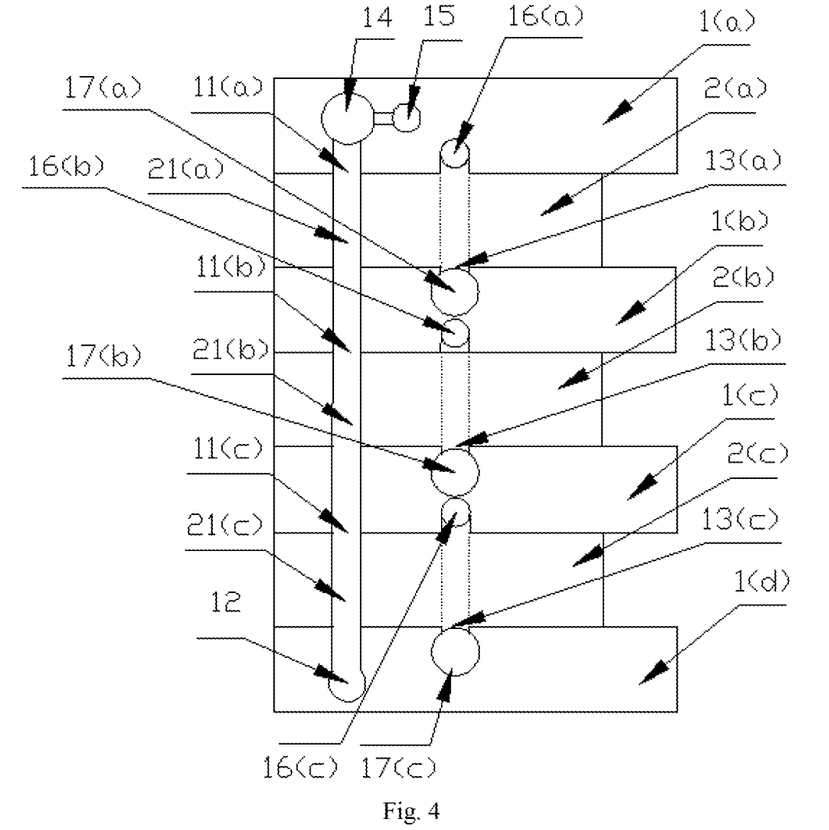
FIG. 4 is a structural schematic diagram of Example 4 of the microfluidic mechanism of the present invention.

FIG. 4 is another preferred example of the core portion of the microfluidic mechanism of the present invention. Example 4 differs from Example 1 in that the microfluidic mechanism is provided with four bases 1 (indicated as 1(a), 1(b), 1(c) and 1(d) in FIG. 4) and three quantitative mechanisms 2 (indicated as 2(a), 2(b) and 2(c) in FIG. 4) arranged alternately, between which six mutual fitting surfaces are formed; the three quantitative mechanisms 2 may horizontally move along the fitting surfaces; wherein, a lower surface of the base 1(a) fits with an upper surface of the quantitative mechanism (2a); a lower surface of the quantitative mechanism (2a) fits with an upper surface of the base (1b); a lower surface of the base 1(b) fits with an upper surface of the quantitative mechanism (2b); a lower surface of the quantitative mechanism (2b) fits with an upper surface of the base (1c); a lower surface of the base 1(c) fits with an upper surface of the quantitative mechanism (2c); and a lower surface of the quantitative mechanism (2c) fits with an upper surface of the base (1d).

Fluid input ends 11 (respectively indicated as 11(a), 11(b) and 11(c) in FIG. 4) are disposed at the lower surfaces of the base 1(a), the base 1(b) and the base 1(c); virtual connecting lines of centers of the three fluid input ends 11 are perpendicular to the quantitative mechanisms 2; the fluid input end 11(a) is provided with a pipeline extending upward and connected with a fluid storage device 14; and the fluid storage device 14 is connected with a first differential pressure mechanism 15.

The quantitative mechanism 2(a) is provided with a quantitative pipeline 21(a); the quantitative mechanism 2(b) is provided with a quantitative pipeline 21(b); the quantitative mechanism 2(c) is provided with a quantitative pipeline 21(c); the quantitative pipeline 21(a), the quantitative pipeline 21(b) and the quantitative pipeline 21(c) are connected with fluid input pipelines, correspondingly penetrating through the base 1(b) and the base 1(c), through the fluid input end 11(b) and the fluid input end 11(c); an upper end of the quantitative pipeline 21(a) is connected with the fluid input end 11(a); and in addition, corresponding to the fluid storage device 14, a waste liquid container 12 is disposed at the base 1(d), and connected with the quantitative pipeline 21(c) above through the extending pipeline, so that the fluid storage device 14 is connected with the waste liquid container 12 through a tandem connection pipeline formed by the three fluid input ends 11 and the three quantitative pipelines 21 which are disposed in a spaced manner.

The fluid receiving ends 13 (indicated as 13(a), 13(b) and 13(c) respectively) are disposed at the upper surfaces of the base 1(b), the base 1(c) and the base 1(d); virtual connecting lines of centers of the three fluid receiving ends 13 are also perpendicular to the quantitative mechanisms 2; the three fluid receiving ends 13(a), 13(b) and 13(c) are provided with pipelines extending downward; the extending pipelines are connected with fluid receiving devices 17(a), 17(b) and 17(c) respectively; and pumps are correspondingly disposed at portions, corresponding to the fluid receiving devices 17 in perpendicular directions, of the bases 1(a), 1(b), 1(c) and 1(d), and act as second differential pressure mechanisms (indicated as 16(a), 16(b) and 16(c) in FIG. 4).

The fluid input ends 11 and the fluid receiving ends 13 are disposed in a staggered manner so that connecting lines between the fluid input ends 11 and the fluid receiving ends 13 are not overlapped with the quantitative pipelines 21 when the quantitative mechanisms 2 slide to any positions.

Operation processes of the microfluidic mechanism are as follows: when the quantitative mechanisms 2(a), 2(b) and 2(c) slide to be in butt joint with the fluid input ends 11 (at positions shown as full lines in FIG. 4) and the three fluid input ends 11(a), 11(b) and 11(c), the extending pipelines of the three fluid input ends 11(a), 11(b) and 11(c) and the plurality of quantitative pipelines 21 are arranged in a spaced manner to form a tandem connection passage, the first relative state is formed; and at this time, under the action of the pressurizing pump as the first differential pressure mechanism 15, the fluid in the fluid storage device 14 flows through the first fluid input end 11(a), the first quantitative pipeline 21(a), the second fluid input end 11(b), the second quantitative pipeline 21(b), the third fluid input end 11(c) and the third quantitative pipeline 21(c) and fills the tandem connection passage up, and an excess portion of the fluid flows into the waste liquid container 12.

Subsequently, the quantitative mechanisms 2(a), 2(b) and 2(c) slide again, the three quantitative pipelines 21 filled with the fluid are pushed to move till the quantitative pipeline 21(a) is connected with the fluid receiving end 13(a), the quantitative pipeline 21(b) is connected with the fluid receiving end 13(b) and the quantitative pipeline 21(c) is connected with the fluid receiving end 13(c) (that is, the quantitative pipelines 21 move to positions shown as dotted lines in FIG. 4), and at this time, the microfluidic mechanism is in the second relative state; in the second relative state, a lower end of each quantitative pipeline 21 is connected with the corresponding fluid receiving end 13, and upper ends of the quantitative pipelines 21 are connected with the pumps (indicated as 16(a), 16(b) and 16(c) in FIG. 4) as the second differential pressure mechanisms 16 of the bases correspondingly located above; and under the action of the pumps, the fluid is pressed out and output to the fluid receiving devices 17 (indicated as 17(a), 17(b) and 17(c) in FIG. 4) through the corresponding fluid receiving ends 13 (indicated as 13(a), 13(b) and 13(c) in FIG. 4).

Example 5

Figure 5:
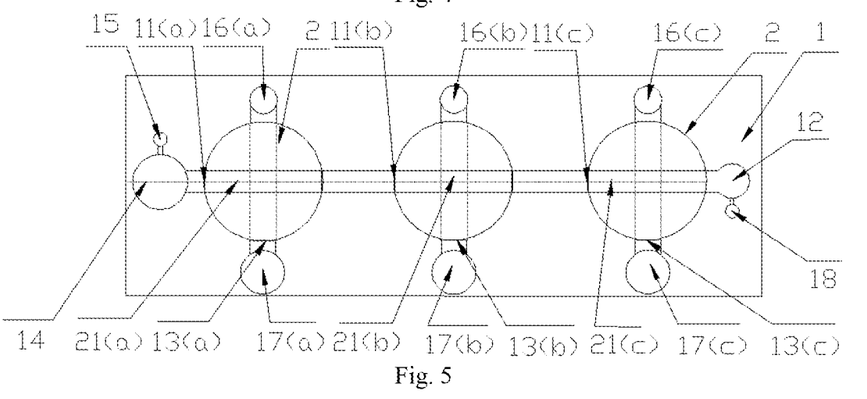
FIG. 5 is a structural schematic diagram of Example 5 of the microfluidic mechanism of the present invention.

FIG. 5 is another preferred example of the core portion of the microfluidic mechanism of the present invention, including a base 1 and a quantitative mechanism 2 which are movably connected. Example 5 differs from Example 1 in that the base 1 is a whole instead of being divided into an upper portion and lower portion; the microfluidic mechanism is provided with three fluid input ends 11 (indicated as 11(a), 11(b) and 11(c) in FIG. 5) and three fluid receiving ends 13 (indicated as 13(a), 13(b) and 13(c) in FIG. 5), which are disposed on the same base; the microfluidic mechanism is provided with three quantitative mechanisms 2 which are rotary discs embedded into the base 1; each quantitative mechanism 2 is provided with one quantitative pipeline 21 disposed in a diameter direction of the rotary disc; and the thicknesses of the rotary discs are greater than the diameters of the quantitative pipelines 21.

Since the rotary discs are embedded into the base 1, the base 1 has vacant spaces corresponding to outlines of the rotary discs, that is, the base 1 has certain flat cylindrical vacant spaces which define side surfaces and circular bottom surfaces of cylinders sunken into the base 1; and the fluid input ends 11 are located at the cylindrical side surfaces (namely surfaces fitting with the rotary discs) of the base 1. In Example 5, the microfluidic mechanism has the three quantitative mechanisms 2 (namely the rotary discs), the three fluid input ends 11 and the three fluid receiving ends 13; as shown in FIG. 4, the three fluid input ends 11 (11(a), 11(b), 11(c)) are disposed directly to left sides of the rotary discs, and the three fluid receiving ends 13 (13(a), 13(b), 13(c)) are disposed directly below the rotary discs; the three fluid input ends 11 have pipelines extending directly to left sides; a pipeline is disposed directly to a right side of the cylindrical side surface, fitting with one rotary disc at the end (the one at the rightmost side), of the base 1, and is further connected with a waste liquid container 12; and the waste liquid container 12 is further provided an exhaust port 18.

The extending pipeline of the first fluid input end 11(a) is connected with a fluid storage device 14; and the fluid storage device 14 is connected with a pressurizing pump as a first differential pressure mechanism 15.

The extending pipeline of each fluid receiving end 13 (13(a), 13(b), 13(c)) is connected with a fluid receiving device 17 (indicated as 17(a), 17(b) and 17(c) in FIG. 5) as a fluid receiving device; pipelines connected with pumps (as second differential pressure mechanisms 16, indicated as 16(a), 16(b) and 16(c) in FIG. 5) are disposed on portions, above portions of the rotary discs on opposite sides of the fluid receiving ends 13, of the base 1; and ports of the pipelines connected with the pumps and the respective fluid receiving ends 13 are in identical perpendicular lines.

During operation, in an initial state, the three quantitative mechanisms 2 (rotary discs) are rotated to positions where the three quantitative pipelines 21 are in a horizontal straight line; the various quantitative pipelines 21 are in butt joint with the respective fluid input ends 11; the pore sizes of the various quantitative pipelines 21 are identical with the sizes of openings of the corresponding fluid input ends 11; as a full line mode shown in FIG. 5, the first fluid input end 11(a) is connected with a left end of the first quantitative pipeline 21(a); a right end of the first quantitative pipeline 21(a) is connected with the leftward extending pipeline of the second fluid input end 11(b); the second fluid input end 11(b) is connected with a left end of the second quantitative pipeline 21(a); a right end of the second quantitative pipeline 21(b) is connected with the leftward extending pipeline of the second fluid input end 11(b); the third fluid input end 11(c) is connected with a left end of the third quantitative pipeline 21(c); a right end of the third quantitative pipeline 21(c) is connected with the waste liquid container 12 through the extending pipeline; at this time, the system is in the first relative state; the plurality of fluid input ends 11, the extending pipelines of the fluid input ends 11 and the plurality of quantitative pipelines 21 already form a tandem connection passage, so that the system carries out continuous fluid charging.

At this time, under the action of the pressurizing pump, the fluid flows through the first fluid input end 11(a), the first quantitative pipeline 21(a), the second fluid input end 11(b), the second quantitative pipeline 21(b), the third fluid input end 11(c) and the third quantitative pipeline 21(c) and fills the tandem connection passage up, and an excess portion of the fluid flows into the waste liquid container 12.

Subsequently, the quantitative mechanisms 2 are rotated again, the quantitative pipelines 21 filled with the fluid are rotated by 90 degrees, and when the quantitative pipeline 21(a) is connected with the fluid receiving end 13(a), the quantitative pipeline 21(b) is connected with the fluid receiving end 13(b) and the quantitative pipeline 21(c) is connected with the fluid receiving end 13(c), the microfluidic mechanism is in the second relative state, that is, the quantitative pipelines 21 in FIG. 5 move from a full line mode to a dotted line mode; in the second relative state, a lower end of each quantitative pipeline 21 is connected with the corresponding fluid receiving end 13 (that is, the quantitative pipeline 21(a) is connected with the fluid receiving end 13(a), the quantitative pipeline 21(b) is connected with the fluid receiving end 13(b) and the quantitative pipeline 21(c) is connected with the fluid receiving end 13(c)); upper ends of the quantitative pipelines 21 correspond to the pumps (namely 16(a), 16(b) and 16(c) respectively) as the second differential pressure mechanisms 16 above the rotary discs; and under the action of the pumps, the fluid is pressed out and output to the fluid receiving devices 17 (17(a), 17(b), 17(c)) through the fluid receiving ends 13 (13(a), 13(b), 13(c)).

Example 6

Figure 6:
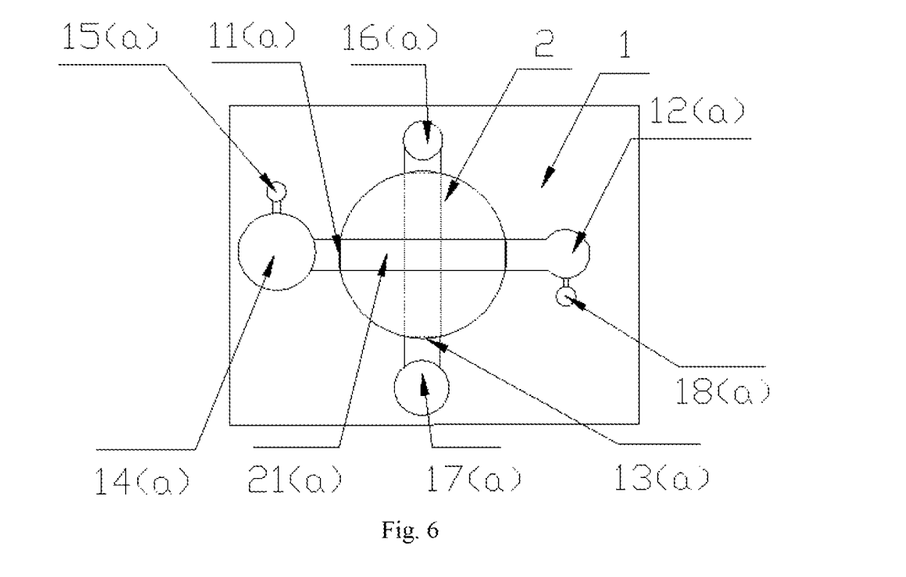
FIG. 6 is a front view of a structural schematic diagram of Example 6 of the microfluidic mechanism of the present invention.
Figure 7:
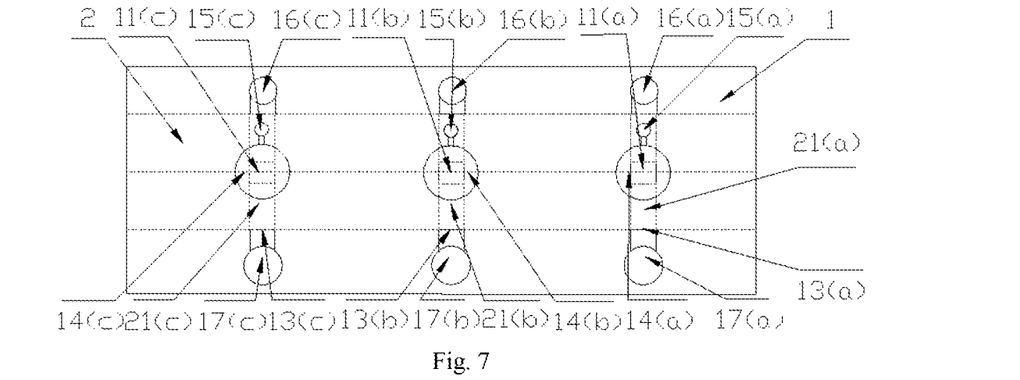
FIG. 7 is a left view of the structural schematic diagram of Example 6 of the microfluidic mechanism of the present invention.
Figure 8:
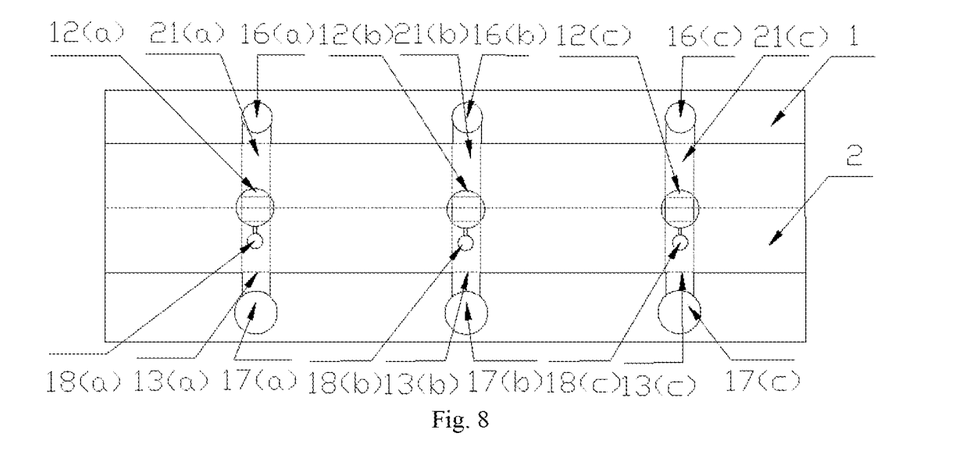
FIG. 8 is a right view of the structural schematic diagram of Example 6 of the microfluidic mechanism of the present invention.

Example 6 is an embodiment in which, on the basis of Example 5, the quantitative mechanisms 2 which utilize one rotary disc to rotate to drive one quantitative pipeline 21 is turned into rotary drums capable of driving a plurality of quantitative pipelines 21 to rotate, as shown in a front view FIG. 6, a left view FIG. 7 and a right view FIG. 8. Example 6 differs from Example 5 in that the quantitative mechanisms 2 are rotary drums embedded into the base 1.

Correspondingly, cylindrical vacancies corresponding to outlines of the rotary drums are disposed on the base 1; and the fluid input ends 11 are located at the cylindrical side surfaces (namely surfaces fitting with the rotary drums). In example 6, corresponding to the three quantitative pipelines 21 (indicated as 21(a), 21(b) and 21(c) in the figures), the microfluidic mechanism is provided with three fluid input ends 11 (indicated as 11(a), 11(b) and 11(c) in the figures), three fluid receiving ends 13 (indicated as 13(a), 13(b) and 13(c) in the figures) and three waste liquid containers 12 (indicated as 12(a), 12(b) and 12(c) in the figures); each group of quantitative pipeline 21, fluid input end 11, fluid receiving end 13 and waste liquid container 12 is disposed as shown in FIG. 6, that is, the three fluid input ends 11 are disposed directly to left sides of the rotary drums, the three fluid receiving ends 13 are disposed directly below the rotary drums, and the three waste liquid containers 12 are connected with pipelines extending directly to right sides of the rotary drums; the waste liquid containers 12 are further provided with exhaust ports 18; and a plane where a center of each group of the mechanisms above is tangent with the cross section of a cylinder of the corresponding rotary drum.

On such basis, referring to Example 2, the microfluidic mechanism is connected with fluid storage devices 14, pumps as first pressure difference mechanisms 15, pumps as second pressure difference mechanisms 16, and fluid receiving devices 17 as the fluid receiving devices through pipelines correspondingly, which are disposed in the same directions as the foregoing example, as shown in FIG. 6.

During operation, in an initial state, the quantitative mechanisms 2 (rotary drums) drive three quantitative pipelines 21 (indicated as 21(a), 21(b) and 21(c) in figures) to be rotated to be in a horizontal straight line; the various quantitative pipelines 21 are in butt joint with the respective fluid input ends 11; the pore sizes of the various quantitative pipelines 21 are identical with the sizes of openings of the corresponding fluid input ends 11, as a dotted line mode shown in FIG. 6; the fluid input end 11(a) is connected with a left end of the quantitative pipeline 21(a); a right end of the quantitative pipeline 21(a) is connected with the waste liquid container 12(a) through the extending pipeline; the remaining two groups are also in such connection state at the same time; and at this time, the system is in the first relative state and can carry out fluid charging.

At this time, under the action of a pressurizing pump, the fluid fills the connected pipelines up through the various fluid input ends 11 via the corresponding quantitative pipelines 21, and an excess portion of the fluid then flows into the corresponding waste liquid containers 12 (indicated as 12(a), 12(b) and 12(c) in the figures).

Subsequently, the quantitative mechanisms 2 (rotary drums) are rotated again to drive the three quantitative pipelines 21 filled with the fluid to be simultaneously rotated by 90 degrees, and when the quantitative pipeline 21(a) is connected with the fluid receiving end 13(a), the quantitative pipeline 21(b) is connected with the fluid receiving end 13(b) and the quantitative pipeline 21(c) is connected with the fluid receiving end 13(c), the microfluidic mechanism is in the second relative state, that is, the quantitative pipelines 21 in FIG. 6 are rotated from a full line mode to a dotted line mode, and the remaining two groups are arranged in the same way; in the second relative state, a lower end of each quantitative pipeline 21 is connected with the corresponding fluid receiving end 13, and upper ends of the quantitative pipelines 21 correspond to the pumps as the second differential pressure mechanisms 16 (indicated as 16(a), 16(b) and 16(c) in figures) above the rotary discs; and under the action of the pumps, the fluid is pressed out and output to the fluid receiving devices 17 (indicated as 17(a), 17(b) and 17(c) in figures) through the fluid receiving ends 13.

Example 7

Example 7 is a microfluidic chip which is a preferred embodiment in which a pretreatment chamber 19 is further connected to a fluid storage device 14 and a filter mechanism 110 is disposed at a connecting portion of the fluid storage device 14 and the pretreatment chamber 19, on the basis of the foregoing example.

Figure 9:
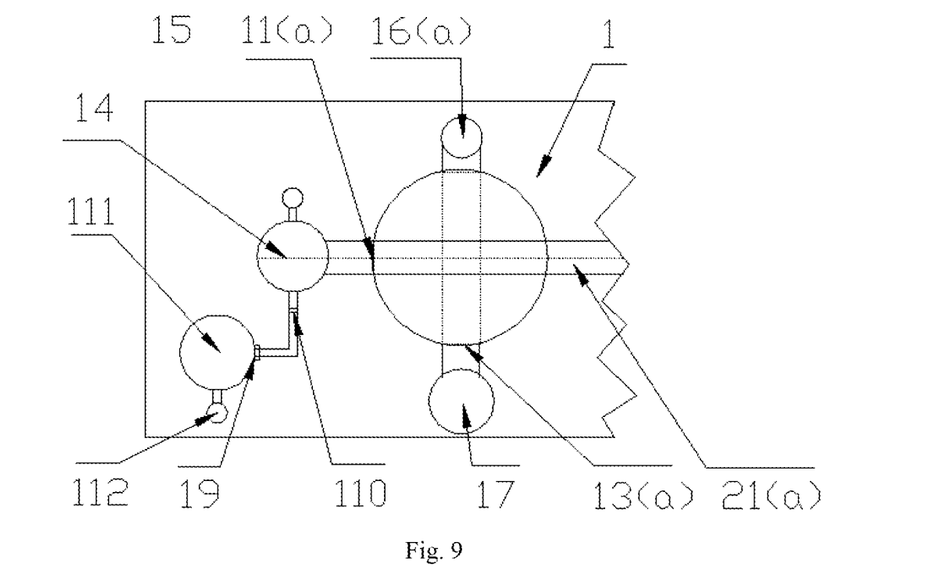
FIG. 9 is a partial view of a microfluidic chip of the present invention.

Example 7 differs from Example 3 in that as shown in FIG. 9, the base 1 is provided with the fluid storage device 14 and the pretreatment chamber 19; the fluid storage device 14 is connected with the pretreatment chamber 19 through a pipeline of a filter sheet 110 acting as the filter mechanism; the left of the pretreatment chamber 19 is further connected with a sample adding device 111; a pressurizing pump 112 is connected directly below the sample adding device 111; the pretreatment chamber 19 is further provided with a heating device (not shown in FIG. 9); and fluid receiving devices 17 connected with the downward extending pipelines of the fluid receiving ends 13 are reaction chambers at the same time.

For example, the rest of the mechanisms are set as in Example 3. During operation, in an initial state, the fluid is pretreated in the pretreatment chamber 19 and heated by the heating device to have a certain temperature required for reaction; the fluid treated by the pretreatment chamber 19 is pressed out of the pretreatment chamber 19 under the action of the pressurizing pump 112; after being filtered by the filter sheet 110 in the pipeline, the fluid flows into the fluid storage device 14, and then flows into the first fluid input end 11(a) under the action of a pressure pump of a first differential pressure mechanism 15; taking the first group of the quantitative pipeline 21(a) and correspondingly disposed mechanisms of the first quantitative pipeline 21(a) as an example, when the mechanisms in the connection modes in the first relative state are filled with the fluid, the rotary discs are clockwise rotated by 90 degrees to the second relative state; and the fluid flows into the reaction chamber to undergo next reaction through the liquid receiving end 13(a) under the pressurizing action of a second differential pressure mechanism 16(a).

Example 8

Figure 10A:
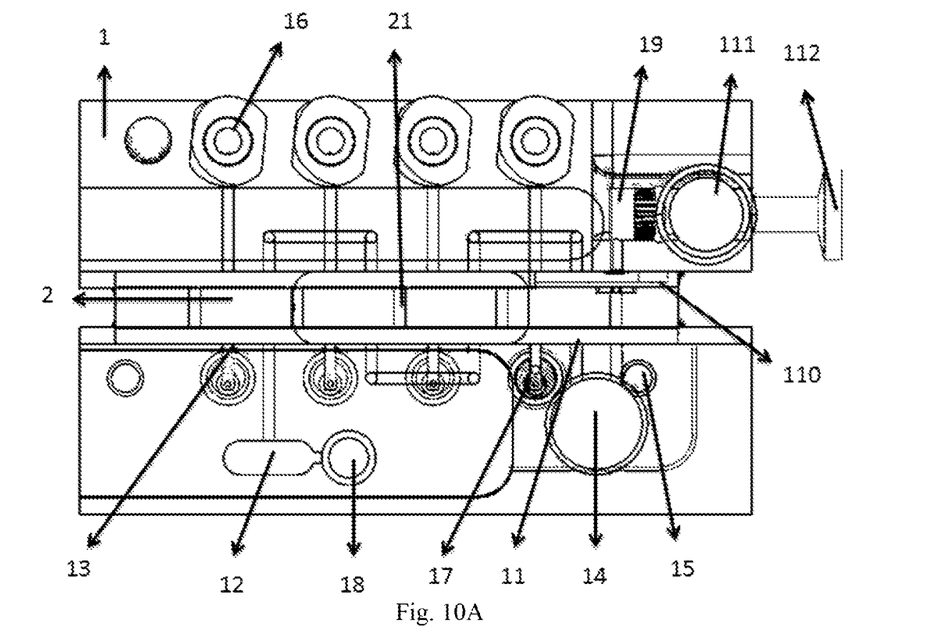
FIGS. 10A-10C are schematic diagrams of another microfluidic chip of the present invention, wherein 10A is a schematic diagram of a pretreatment state, 10B is a schematic diagram of a first relative state, and 10C is a schematic diagram of a second relative state.
Figure 10B:
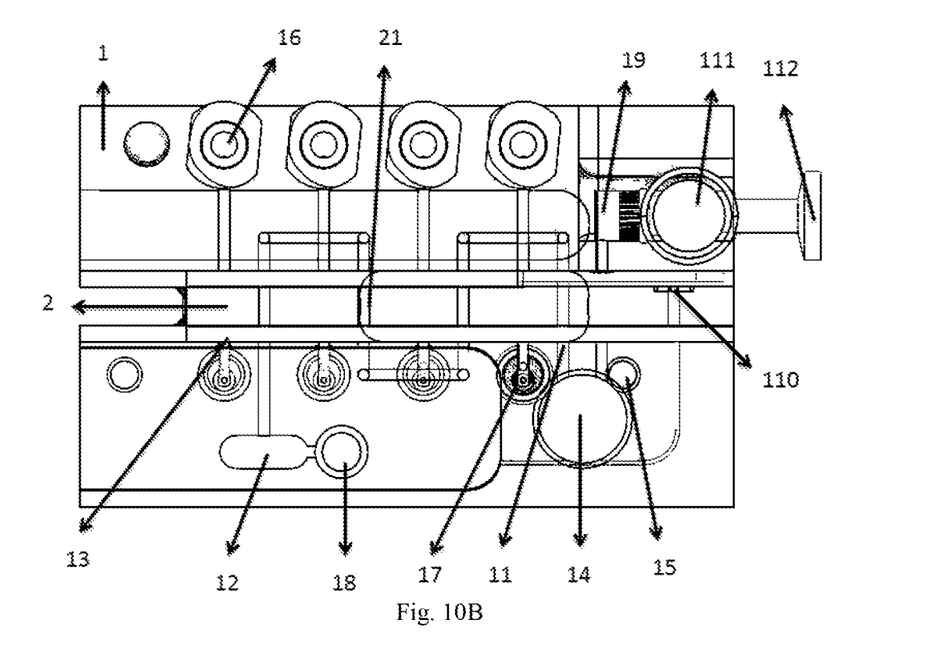
Figure 10C:
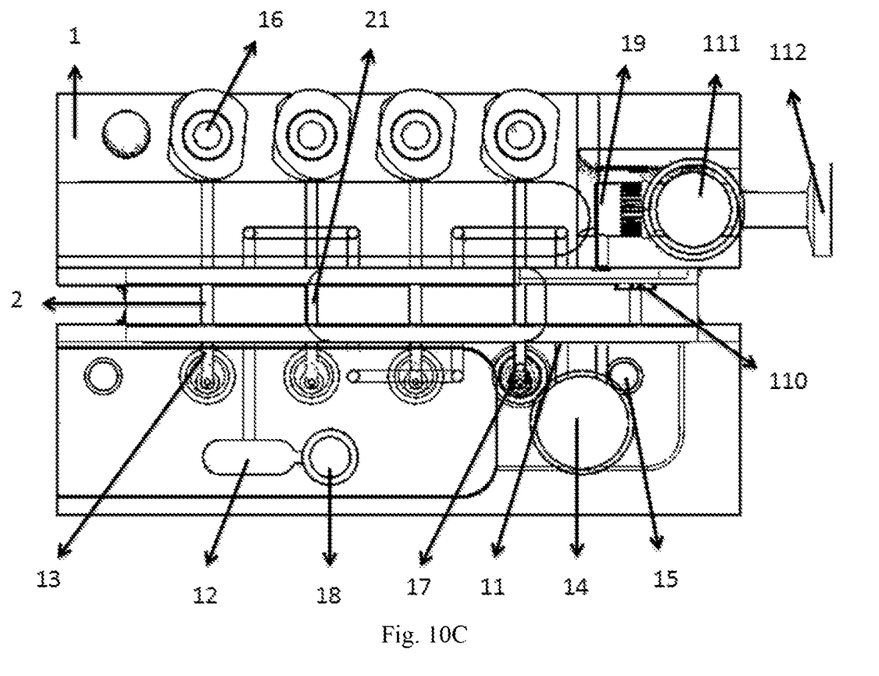

FIG. 10 shows another microfluidic chip. A microfluidic mechanism of this microfluidic chip is similar to that in Example 3, but is provided with four fluid input ends, four fluid receiving ends, four quantitative pipelines, as well as four corresponding first differential pressure mechanisms and pumps and four fluid receiving devices 17 (being reaction chambers simultaneously).

A pretreatment chamber 19 and a fluid storage device 14 are located at a first base and a second base respectively, and the pretreatment chamber 19 is connected with the fluid storage device 14 through a pipeline disposed at a quantitative mechanism 2; a filter mechanism 110 is located on this pipeline; and the pretreatment chamber 19 is provided with a heating device (not shown in FIG. 10).

As shown in FIG. 10A, at this time, a sample enters the pretreatment chamber 19 under the action of the sample adding device 111 and a pressurizing pump 112 of the sample adding device 111, then is subjected to heating pretreatment here and filtered by the filter mechanism 110 and flows into the fluid storage device 14.

Later, the microfluidic chip is in a state as shown in FIG. 10B, at this time, based on the principle of Example 3, the microfluidic mechanism is in a continuous fluid charging state. After the quantitative pipelines 21 are all filled with the fluid, the quantitative mechanism 2 is moved to a next state (FIG. 10C).

In the state as shown in FIG. 10C, the quantitative pipelines 21 are connected with the fluid receiving ends 13 below, and through pressure applied by the second differential pressure mechanisms 16, the fluid flows into the fluid receiving devices 17.

What is claimed is:
1. A fluid control mechanism, comprising:
  a base, comprising:
    a plurality of fluid input ends, comprising:
      a first fluid input end; and
      a second fluid input end; and
    a plurality of fluid receiving ends, comprising:
      a first fluid receiving end in fluid connection with the first fluid input end; and
      a second fluid receiving end not in fluid connection with the second input end; and
  a quantitative mechanism comprising:
    a first pipeline; and
    a second pipeline;
  wherein the quantitative mechanism is movably connected to the base to form two or more interchangeable states including a first state and a second state, wherein
    in the first state, the first pipeline is in fluid connection with the first fluid input end, and the second pipeline is in fluid connection with the first fluid receiving end, thus the first pipeline and the second pipeline are in fluid connection by the fluid connection of the first fluid input end and the first fluid receiving end; and
    in the second state, the first pipeline is in fluid connection with the second fluid input end, and the second pipeline is in fluid connection with the second fluid receiving end.

2. The fluid control mechanism of claim 1, wherein in a switching process between the first state to the second state, two ends of the first and second quantitative pipelines are kept sealed.

3. The fluid control mechanism of claim 1, wherein the base is provided with at least one surface fitting with the quantitative mechanism, and the first and second fluid input ends and the first and second fluid receiving ends are disposed at the fitting surfaces of the base and the quantitative mechanism.

4. The fluid control mechanism of claim 1, wherein in the first state, the second pipeline, the first fluid receiving end, the first fluid input end and the first pipeline define a tandem connection passage.

5. The fluid control mechanism of claim 1, wherein the first state and the second state are capable of interchanged by translational motion or rotational motion.

6. The fluid control mechanism of claim 1, wherein at least one of the first and second fluid input ends are connected with a fluid storage device.

7. The fluid control mechanism of claim 1, is further comprising a first differential pressure mechanism; wherein, in the first state, the first differential pressure mechanism
allows pressure at an end, connected with the first fluid input end, of the first pipeline to be greater than pressure at an end, far away from the first fluid input end, of the first pipeline, and/or
allows pressure at an end, far away from the first fluid receiving end, of the second pipeline to be greater than pressure at an end, connected with the first fluid receiving end, of the second pipeline.

8. The fluid control mechanism of claim 1, further comprising a second differential pressure mechanism; wherein, in the second state, the second differential pressure mechanism
allows pressure at an end, far away from the second fluid input end, of the first pipeline to be less than pressure at an end, connected with the second fluid input end, of the first pipeline, or
allows pressure at an end, connected with the second fluid receiving end, of the second pipeline to be less than pressure at an end, far away from the second fluid receiving end, of the second pipeline.

9. The fluid control mechanism of claim 1, wherein in the first state, an exhaust port is in fluid connection with an end, far away from the first fluid input end, of the first quantitative pipeline.

10. The fluid control mechanism of claim 4, wherein an exhaust port is disposed at a tail end of the tandem connection passage.

11. The fluid control mechanism of claim 1, wherein the fluid input ends and the fluid receiving ends are all disposed at connected surfaces of the base and the quantitative mechanism.

12. The fluid control mechanism of claim 1, wherein cross-sectional areas of the quantitative pipelines are 0.01-100 mm$^2$.

13. The fluid control mechanism of claim 4, wherein the tandem connection passage penetrates through the base and the quantitative mechanism to form a sinuous channel.

14. The fluid control mechanism of claim 4, wherein the quantitative mechanism is two or more rotary discs embedded into the base; a thickness of the rotary discs are greater than diameters of the first and second pipelines.

15. The fluid control mechanism of claim 4, wherein
an end, connected with the first fluid input end, of the first pipeline,
an end, far away from the first fluid input end, of the first pipeline,
an end, far away from the first fluid receiving end, of the second pipeline, and
an end, connected with the first fluid receiving end, of the second pipeline
are arranged on a straight line parallel to the first pipeline and the second pipeline.

16. A system comprising the fluid control mechanism of claim 1, wherein at least one of the plurality of input ends is connected with a fluid storage device; and
the fluid storage device is further connected with a pretreatment chamber.

17. The system of claim 16, wherein the pretreatment chamber is connected with the fluid storage device through a third pipeline.

18. The system of claim 16, wherein
the base comprises a first base and a second base;
wherein,
the pretreatment chamber and the fluid storage device are located at the first base or the second base at the same time, or
the pretreatment chamber and the fluid storage device are located at the first base and the second base respectively, and the pretreatment chamber is connected with the fluid storage device through a fourth pipeline disposed at the quantitative mechanism.

19. The system of claim 16, wherein at least one of the plurality of fluid receiving ends is connected with fluid receiving devices.

20. Use of the fluid control mechanism of claim 1, wherein the fluid control mechanism is used for quantitative sampling or detection of biological samples.

* * * * *